United States Patent [19]

Deeg et al.

[11] Patent Number: 5,068,179
[45] Date of Patent: Nov. 26, 1991

[54] PROCESS FOR THE DETERMINATION OF A COMPONENT OF AN IMMUNE REACTION IN A PLASMA SAMPLE

[75] Inventors: Rolf Deeg, Bernried; Rainer Wehner, Gauting; Johann Mattersberger, Munich; Udo Becker, Marburg, all of Fed. Rep. of Germany

[73] Assignee: Boehringer Mannheim GmbH, Mannheim, Fed. Rep. of Germany

[21] Appl. No.: 262,166

[22] Filed: Oct. 18, 1988

Related U.S. Application Data

[63] Continuation of Ser. No. 900,827, Aug. 27, 1986, abandoned.

[30] Foreign Application Priority Data

Aug. 29, 1985 [DE] Fed. Rep. of Germany ....... 3530942

[51] Int. Cl.$^5$ .................. G01N 33/53; G01N 33/543
[52] U.S. Cl. .................. 435/7.92; 435/7.93; 435/7.94.7.95.962; 435/13; 435/215; 435/216; 435/217; 436/500; 436/518; 436/825
[58] Field of Search ................ 435/7, 13, 215–217, 435/7.92–7.95, 962; 436/500, 518, 825

[56] References Cited

U.S. PATENT DOCUMENTS

| | | |
|---|---|---|
| 4,463,090 | 7/1984 | Harris ..................... 435/7 |
| 4,639,425 | 1/1987 | Baier ..................... 436/518 |
| 4,710,459 | 12/1987 | Barth et al. ............. 435/13 |
| 4,791,068 | 12/1988 | Loskutoff et al. ......... 436/118 |

OTHER PUBLICATIONS

Triplett, D. "Determination of Plasminogen, Plasmin and Plasminogen Activators", *Clin. Lab. Ann.* (1) 273–275, 1982.
Wintrobe et al., *Clinical Hematology*, 1974, pp. 434–435.
White et al., *Principles of Biochemistry*, 1968, pp. 733–734.
Harker, Hemostasis Manual, 2nd edition, pp. 34–36, (1974).
Brosstad, Thrombosis Research, vol. 15; 497–504, (1979).
Davidson et al., Progress in Fibrinolysis, vol. VI, pp. 65, 213 and 219, (1983).
Scully et al., Biochimica et Biophysica Acta, vol. 700, pp. 130–133 (1982).
Gruyter, Concise Encyclopedia of Biochemistry, pp. 163–164 (1983).
Bang et al., Thrombosis and Bleeding Disorders Theory and Methods, pp. 296–297, 300–309 (1971).
Chem. Abst. 103(5): 34357g.
Bergmeyer, Methods of Enzymatic Analysis, vol. 5, p. 425.

*Primary Examiner*—Esther L. Kepplinger
*Assistant Examiner*—Carol A. Spiegel
*Attorney, Agent, or Firm*—Felfe & Lynch

[57] ABSTRACT

The present invention provides a method for the determination of a component of an immune reaction in a plasma sample using an immunoassay at a temperature of from 15° to 40° C., where one of the reactive components is in solid phase. The invention involves adding an amount of plasminogen activator sufficient to eliminate interference by fibrinogen with the component to be determined.

10 Claims, No Drawings

PROCESS FOR THE DETERMINATION OF A COMPONENT OF AN IMMUNE REACTION IN A PLASMA SAMPLE

This application is a continuation of application Ser. No. 900,827, filed Aug. 27, 1986, now abandoned.

The present invention is concerned with a process and a reagent for the determination of a component of an immune reaction in a plasma sample according to the immunoassay principle at a temperature of from 15° to 40° C., one of the reaction components being present in solid phase.

Processes for immunoassays are widely known and include not only processes in the homogeneous phase but also processes in the heterogeneous phase. In the case of processes in the heterogeneous phase, one of the reaction partners is bound to a carrier.

For carrying out an immunoassay in the heterogeneous phase, various process variants are known, for example the sandwich process, the indirect process and the competition process.

In the case of the sandwich process, an antibody is bound to a carrier and a test solution is added, the specific antigen contained in the test solution thereby being bound to the antibody. A labelled specific antibody for the antigen-antibody complex or for parts of the complex is then added which binds to the complex. The amount of antigen can then be calculated via the labelled antibody.

In the case of the indirect process, an antigen is bound to the carrier material. The test solution is added thereto, the antibody specific for the bound antigen contained in the test solution thereby reacting with the antigen. Upon adding a labelled antiglobulin, the antiglobulin binds to the antigen-antibody complex and the amount of the unknown antibody in the test serum can again be determined via the labelled antiglobulin.

In the case of the competition process, one of the components of an immune reaction is bound to the carrier material. There is then added thereto a solution which contains not only the other component of the immune reaction present in unknown amount but also a known amount of labelled other component of the immune reaction. Both components, the labelled and the unlabelled, compete for the binding places of the component of the immune reaction bound on the carrier. To a second sample, is added a standard solution which only contains labelled component. By determination of the labelled component in the standard and in the sample, there can now be calculated the amount of unknown reaction component from the difference.

Further possibilities for a determination are provided in the case of an at least bivalent antigen with the help of three receptors, which can be antibodies or antibody fragments. When carrying out an immunoassay with three receptors in heterogeneous phase, one of the three receptors is always insoluble, whereas the other two are soluble, one of the two soluble receptors being labelled, whereas the other is not labelled. The insoluble receptor is then directed against the non-labelled soluble receptor. For carrying out the determination, various process variants are possible, not only one-step but also multi-step, in which the addition of the individual receptors can be varied.

Thus, a further process variant consists in that an antigen to be determined in a sample is reacted in the first step simultaneously with a soluble, non-labelled receptor and a soluble labelled receptor in solution and then the resulting soluble sandwich complex is made insoluble in a second step by binding to an insoluble receptor.

Various possibilities are known for labelling the reaction components. Thus, one of the reactive components can be radioactively labelled, the measured radioactivity thereby permitting a calculation of the reaction component to be determined. Furthermore, labelling can be carried out with an enzyme. Then, after carrying out the usual steps of the immune determination, there is added a substrate for the enzyme which is used as labelling and then, via its reaction, the concentration of the reaction component to be determined is calculated. A further possibility is labelling with a fluorescing substance: the fluorescence can then be determined directly or with a coloured material, the evaluation taking place spectro- or photometrically.

Immunoassays are of increasing importance since, with the help thereof, on the one hand, substances can be detected very specifically and, on the other hand, they have a very great sensitivity and, with the use of these methods, substances can be detected down to the picogram range. However, immunoassays in a heterogeneous phase are falsified to varying extent by non-analyte-specific interferences, i.e. so-called non-specific disturbances, which have already been called "matrix effect", "background" and "non-specific binding". An especially disturbing effect which makes itself noticeable is that the recovery of the substance to be determined in plasma samples in the sandwich process is distinctly smaller than in the case of serum samples and in the case of competitive processes is distinctly greater than in the case of serum samples.

We have now found that this falsification of the results is caused by fibrinogen, which is present in plasma but not in serum. This disturbance is independent of the nature of the stabilization of the plasma, i.e. added ethylenediamine-tetraacetic acid, citrate, heparin or the like have no influence on the recovery. However, it only occurs in the case of immunoassays in a heterogeneous phase. We have now ascertained that when carrying out a competitive process, fibrinogen simulates the analytes to be determined. This does not take place by cross-reaction but rather because the fibrinogen, which is a surface-active substance, deposits on the surface of the carrier material to which is bound the component of the immune reaction present in solid phase and thus partly covers over the bound component. On the other hand, in the case of the sandwich process, the fibrinogen gives rise to too low values. In order to solve this problem, it has already been suggested to heat plasma samples, before carrying out the immune determinations, for 10 minutes in a waterbath to 56° C. and subsequently to centrifuge. This process is, on the one hand, more laborious and, on the other hand, can only be used when substances are to be determined which are not denatured by this treatment. Furthermore, it has also been suggested to influence the disturbing effect of the fibrinogen by the addition of urea. However, it was thereby found that the influencing is only possible under quite definite conditions and that these conditions must be freshly determined for each individual plasma sample. This process is also very laborious.

Therefore, it is an object of the present invention to provide a process with the help of which it is possible to determine a component of an immune reaction according to the immunoassay principle in which one of the reaction components is present in solid phase, which process is also applicable to plasma samples without laborious process steps being necessary therefor. Furthermore, it is an object of the present invention to provide a reagent which can be used for immunoassays in plasma samples.

Thus, according to the present invention, there is provided a process for the determination of a component of an immune reaction in a plasma sample according to the immunoassay principle at a temperature of from 15° to 40° C., one of the reaction components being present in solid phase, wherein a fibrinolytically-effective agent is added to the incubation medium of the immune reaction.

Surprisingly, we have ascertained that an addition of a fibrinolytically-effective agent to the incubation medium in an immune determination improves the recovery so that the values which are obtained from plasma samples agree substantially with those which are obtained from serum samples. This was surprising since this improvement occurs in the case of the usual carrying out of the process, i.e. with the usual incubation times and incubation temperatures. From the literature, it was already known that the breakdown of fibrinogen by means of fibrinolytically-effective agents requires long incubation times and comparatively high temperatures. However, with the process according to the present invention, it is possible, without carrying out further process steps, to improve the immune determination in plasma samples by simple admixing.

The process can be employed for all types of plasma. Thus, it can be used not only for plasma which, for stabilization, has been mixed with ethylene-diamine-tetraacetic acid (EDTA) but also for plasma which has been stabilized with heparin, citrate, oxalate, fluoride or similar substances.

An influencing of the immune determination by the fibrinolytically-effective agent does not occur so that, by means of the addition according to the present invention, no falsification of the values takes place.

The process according to the present invention can be used not only for one-step processes but also for two-step determination processes. It is thereby preferred, in the case of two-step processes, to add the fibrinolytic agent at the first incubation since the plasma sample is already added at the first incubation stage and thus the fibrin or fibrinogen causing the disturbance is introduced.

A plasminogen activator is preferably added as fibrinolytically-effective agent. By the action of the plasminogen activator, the plasminogen present in the sample is converted into plasmin which then proteolytically breaks down the fibrinogen.

As plasminogen activator, it is especially preferred to use streptokinase or urokinase. The streptokinase is preferably added in an amount of from 10 to 300 U/ml. and especially preferably of from 40 to 150 U/ml. In the case of smaller amounts, the action no longer occurs to the full extent. Amounts greater than 300 U/ml. do not further improve the recovery and are, therefore, uneconomic.

The urokinase is preferably added in an amount of from 10 to 120 U/ml. and especially preferably of from 20 to 80 U/ml. Here, too, in the case of smaller amounts, the action is, under certain circumstances, no longer quite sufficient, whereas concentrations above the upper limit are unnecessary.

In a further preferred embodiment of the process according to the present invention, as fibrinolytically-effective agent, there is added to the incubation medium of the immune reaction extrinsic plasminogen activator (EPA). The EPA is preferably added in an amount of from 0.2 to 10 μg./ml. and especially preferably of from 0.5 to 3 μg./ml.

The process according to the present invention is applicable to all kinds of immunoassays in which one of the reaction components is present in solid phase. Thus, it can be used for competitive and for sandwich processes and for all kinds of labellings.

For carrying out the process according to the present invention, there can be used a reagent which, besides the usual component materials, also contains a fibrinolytic agent. The reagent preferably also contains a buffer substance, for example phosphate buffer, citrate buffer, borate buffer and the like and/or bovine serum albumin and/or a preserving agent. If an enzyme is used as labelling, then the reagent also contains a system for the detection of the enzyme activity.

As fibrinolytically-effective agent, the reagent according to the present invention preferably contains a plasminogen activator, streptokinase, urokinase and EPA being preferred as plasminogen activators. The reagent preferably contains 10 to 300 U/ml. and especially preferably 40 to 150 U/ml. streptokinase or preferably contains 10 to 120 U/ml. and especially preferably 20 to 80 U/ml. urokinase or preferably contains 0.2 to 10 μg./ml. and especially preferably 0.6 to 3 μg./ml. EPA.

The following Example is given for the purpose of illustrating the present invention:

EXAMPLE

| Solution 1. Incubation buffer | |
|---|---|
| phosphate buffer | 15 mmol/liter (pH 6.9) |
| bovine serum albumin (BSA) | 0.2% by weight |
| merthiolate | 0.01% by weight |
| Solution 2. | |
| conjugate of antibody to thyroid stimulating hormone and peroxidase (anti-TSH-POD) dissolved in Solution 1 | about 40 U/l. |
| Solution 3. Substrate/buffer solution. | |
| phosphate-citrate buffer | 95 mmol/liter (pH 4.4) |
| sodium perborate | 3.1 mmol/liter |
| 2,2'-azino-d-[3-ethylbenz-thiazoline-6-sulphonic acid] diammonium salt | 1.6 mmol/liter. |

The solutions used, coated test tubes and standards originate from the Enzymun-Test ® TSH (Boehringer Mannheim GmbH, Order No. 73 60 83). The carrying out of the determination takes place analogously to the instructions of the manufacturer.

Into test tubes coated with anti-TSH antibodies are introduced, in each case, 0.2 ml. TSH standard (0 to 50 μU/ml.) or sample material (serum, plasma) and 1 ml. Solution 1 and incubated for 60 minutes at 20° to 25° C. Solution 1 has differing concentrations of urokinase (0 to 70 U/ml.) or of streptokinase (0 to 50 U/ml.) added thereto. After sucking out and rinsing, 1 ml. of Solution 2 is added thereto. After 60 minutes incubation at 20° to 25° C., the test tubes are sucked out and rinsed. Subsequently, 1 ml. of Solution 3 is added thereto and again incubated for 60 minutes at 20° to 25° C. Thereafter, there is carried out, against Solution 3 as blank, a photometric determination at $\lambda = 405$ nm.

The values set out in the following tables are, in each case, referred to the relative value of 100% which was obtained for serum without the addition of urokinase or striptokinase to the incubation buffer.

| | Enzymun-Test ® TSH Addition of urokinase | | |
|---|---|---|---|
| urokinase conc. (U/ml.) | human serum (= reference) | heparin plasma | EDTA plasma |
| 0 | 100% | 58% | 62% |
| 10 | 96% | 72% | 70% |
| 20 | 96% | 88% | 96% |
| 30 | 97% | 91% | 93% |
| 40 | 94% | 92% | 95% |
| 50 | 99% | 97% | 103% |
| 60 | 100% | 104% | 123% |
| 70 | 86% | 95% | 107% |

| | Enzymun-Test ® TSH Addition of streptokinase | | |
|---|---|---|---|
| streptokinase conc. (U/ml.) | human serum (= reference) | heparin plasma | EDTA plasma |
| 0 | 100% | 49% | 52% |
| 0.1 | 98% | 49% | 56% |
| 10 | 103% | 72% | 68% |
| 25 | 94% | 78% | 70% |
| 40 | 106% | 93% | 85% |
| 50 | 106% | 95% | 89% |
| 60 | 100% | 99% | 87% |
| 70 | 106% | 98% | 90% |
| 80 | 100% | 99% | 93% |

| | -continued Enzymun-Test ® TSH Addition of streptokinase | | |
|---|---|---|---|
| streptokinase conc. (U/ml.) | human serum (= reference) | heparin plasma | EDTA plasma |
| 100 | 102% | 102% | 103% |
| 150 | 100% | 99% | 96% |

We claim:

1. In a method for carrying out a heterogeneous immunoassay for a component of a plasma sample at a temperature of from 15°–40° C. in an incubation medium, the improvement comprising adding an amount of a plasminogen activator to said sample sufficient to eliminate interference by fibrinogen with said component to be determined.

2. Method of claim 1, wherein said plasminogen activator is streptokinase.

3. Method of claim 1, wherein said plasminogen activator is urokinase.

4. Method of claim 1, wherein said plasminogen activator is extrinsic plasminogen activator.

5. Method of claim 2, wherein said streptokinase is added in an amount ranging from 10 U to 300 U per ml of incubation medium.

6. Method of claim 2, wherein said streptokinase is added in an amount ranging from 40 U to 150 U per ml of incubation medium.

7. Method of claim 3, wherein said urokinase is added in an amount ranging from 10 U to 120 U per ml of incubation medium.

8. Method of claim 3, wherein said urokinase is added in an amount ranging from 20 U to 80 U per ml of incubation medium.

9. Method of claim 4, wherein said extrinsic plasminogen activator is added in an amount ranging from 0.2 to 10 ug per ml of incubation medium.

10. Method of claim 4, wherein said extrinsic plasminogen activator is added in an amount ranging from 0.5 to 3 ug per ml of incubation medium.

* * * * *